United States Patent
Friedman et al.

(10) Patent No.: US 10,448,868 B2
(45) Date of Patent: Oct. 22, 2019

(54) SYSTEMS AND METHODS FOR MONITORING HAND AND WRIST MOVEMENT

(71) Applicants: Nizan Friedman, Irvine, CA (US); Justin Rowe, Irvine, CA (US); David J. Reinkensmeyer, Irvine, CA (US); Mark G. Bachman, Irvine, CA (US)

(72) Inventors: Nizan Friedman, Irvine, CA (US); Justin Rowe, Irvine, CA (US); David J. Reinkensmeyer, Irvine, CA (US); Mark G. Bachman, Irvine, CA (US)

(73) Assignee: The Regents of the University of California, Oakland, CA (US)

( * ) Notice: Subject to any disclaimer, the term of this patent is extended or adjusted under 35 U.S.C. 154(b) by 55 days.

(21) Appl. No.: 14/203,455

(22) Filed: Mar. 10, 2014

(65) Prior Publication Data
US 2014/0257143 A1     Sep. 11, 2014

Related U.S. Application Data

(60) Provisional application No. 61/774,881, filed on Mar. 8, 2013.

(51) Int. Cl.
*A61B 5/11*     (2006.01)
*A61B 5/00*     (2006.01)

(52) U.S. Cl.
CPC ........... *A61B 5/1126* (2013.01); *A61B 5/1118* (2013.01); *A61B 5/1122* (2013.01); *A61B 5/6825* (2013.01)

(58) Field of Classification Search
CPC .............................. A61B 5/6826; A61B 5/1126
See application file for complete search history.

(56) References Cited

U.S. PATENT DOCUMENTS

| 5,562,448 | A | 10/1996 | Mushabac | |
| 6,050,931 | A * | 4/2000 | Russell | A61N 2/06 600/15 |
| 7,038,658 | B2 * | 5/2006 | Seki | G06F 3/0346 341/21 |
| 2006/0137396 | A1 * | 6/2006 | Ma | A44C 5/00 63/15 |
| 2007/0032748 | A1 * | 2/2007 | McNeil | A61B 5/1038 600/595 |

(Continued)

OTHER PUBLICATIONS

Uswatte, et al., Validity of Accelerometry for Monitoring Real-World Arm Activity in Patients with Suacute Stroke: Evidence from the Extremity Constraint-Induced Therapy Evaluation Trial, Archives of Physical Medicine and Rehabilitation, vol. 87, No. 10. pp. 1340-1345, Oct. 2006.
B. Place, Introduction to Radial Basis Function Networks, Time, pp. 1-67, 1996.
Williams, et al., A Goniometric Glove for Clinical Hand Assessment, Journal of Hand Surgery British and European Volume, vol. 25, No. 2, pp. 200-207, 2000.
Zimmerman, et al., A Hand Gesture Interface Device, ACM SIGCHI Bulletin, vol. 18, No. 4, pp. 189-192, 1987.

(Continued)

*Primary Examiner* — Daniel L Cerioni
*Assistant Examiner* — Yasmeen S Warsi
(74) *Attorney, Agent, or Firm* — Thomas | Horstemeyer, LLP

(57) ABSTRACT

In one embodiment, a system includes apparatus for monitoring hand or wrist movement, the apparatus including a magnetic ring adapted to be worn on a finger of a patient and a data acquisition unit adapted to be worn on a wrist of the patient, the data acquisition unit including a magnetic sensor that can measure the strength and orientation of magnetic fields generated by the ring.

13 Claims, 6 Drawing Sheets

(56) References Cited

U.S. PATENT DOCUMENTS

| | | | | |
|---|---|---|---|---|
| 2009/0204031 A1* | 8/2009 | McNames | ............ | A61B 5/1071<br>600/595 |
| 2010/0145236 A1* | 6/2010 | Greenberg | ........... | A61B 5/1101<br>600/595 |

OTHER PUBLICATIONS

Simone, et al., A Low Cost Instrumented Glove for Extended Monitoring and Functional Hand Assessment, Journal of Neuroscience Methods, vol. 160, No. 2, pp. 335-348, Mar. 2007.
Seitz, et al., Spontaneous Arm Movement Activity Assessed by Accelerometry is a Marker for Early Recovery and Stroke, Journal of Neurology, vol. 258, No. 3, pp. 457-463, Mar. 2011.
Patel, et al., A Novel Approach to Monitor Rehabilitation Outcomes in Stroke Survivors Using Wearable Technology, Proceedings of the IEEE, vol. 98, No. 3, pp. 450-461, Mar. 2010.
Yang, et al., A Review of Accelerometry-Based Wearable Motion Detectors for Physical Activity Monitoring, Sensors (Petersboroug, vol. 10, No. 8, pp. 7772-7788, 2010.
Patel, et al., A Review of Wearable Sensors and Systems with Application in Rehabilitation, Journal of Neuroengineering and Rehabilitation, vol. 9, No. 1, p. 21, Jan. 2012.
Sturman, et al., A Survey of Glove-Based Input, Computer Graphics and Applications IEEE, vol. 14, No. 1, pp. 30-39, 1994.
Haeuber, et al., Accelerometer Monitoring of Home and Community Based Ambulatory Activity After Stroke, Archives of Physical Medicine and Rehabilitation, vol. 85, No. 12, pp. 1997-2001, 2004.
Bassett, et al., Accurancy of Five Electronic Pedometers for Measuring Distance Walked, Medicine & Science in Sports and Exercise, vol. 28, No. 8, pp. 1071-1077, 1996.
Lang, et al., Assessment of Upper Extremity Impairment, Function, and Activity After Stroke: Foundations for Clinical Decision Making, Journal of Hand Therapy: Offical Journal of the American Society of Hand Therapists, Sep. 2012.
Renaudin, et al. Complete Triaxis Magnetometer Calibration in the Magnetic Domain, Journal of Sensors, vol. 2010, pp. 1-10, 2010.
Markovsky, et al., Consistent Least Squares Fitting of Ellipsoids, Numerische Mathematik, vol. 98, No. 1, Apr. 2004.
Fahn, et al., Development of a Fingertip Glove Equipped with Magnetic Tracking Sensors, Sensors (Basel, Switzerland), vol. 10, No. 2, pp. 1119-1940, Jan. 2010.
Mitobe, et al., Development of a Motion Capture System for a Hand Using Magnetic Three Dimensional Position Sensor, ACM SIGGRAPH 2006, Research Posters on SIGGRAPH, 2006, p. 102.
Godfrey, et al., Direct Measurement of Human Movement by Accelerometry, Medical Engineering and Physics, vol. 30, No. 10, pp. 1364-1386, 2008.
Bonato, et al., Advances in Wearable Technology and Applications in Physical Medicine and Rehabilitation, Journal of Neuroengineering and Rehabilitation, vol. 2, No. 1, p. 2, Feb. 2005.
Van Galen, et al., Effects of Motor Programming on the Power Spectral Density Function of Finger and Wrist Movements, Journal of Experimental Psychology: Human Perception and Performance, vol. 16, No. 4, pp. 755-765, 1990.
Wahlstrom, Ergonomics, Musculoskeletal Disorders and Computer Work, Occupational Medicine (Oxford, England), vol. 55, No. 3, pp. 168-176, May 2005.
Feito, et al., Evaluation of Activity Monitors in Controlled and Free-Living Environments, Medicine and Science in Sports and Exercise, vol. 44, No. 4, pp. 733-741, Apr. 2012.
Phillips, et al., Finger Mobility Following Flexor Tendon Repair, Journal of Hand Surgery (Edinburgh, Scotland), vol. 10, No. 3, pp. 337-339, Oct. 1985.
Rand, et al., How Active are People with Stroke?: Use of Accelerometers to Assess Physical Activity, Stroke: A Journal of Cerebral Circulation, vol. 40, No. 1, pp. 163-168, Jan. 2009.

Dennerlein, et al., Different Computer Tasks Affect the Exposure of the Upper Extremity to Biomechanical Risk Factors, Ergonomics, vol. 49, No. 1, pp. 45-64, Jan. 2006.
Karantonis, et al., Implementation of a real-time human movement classifier Using a Triaxial Accelerometer for Ambulatory Monitoring, IEEE Transactions on Information Technology in Biomedicine a Publication of the IEEE Engineering in Medicine and Biology Society, vol. 10, No. 1, pp. 156-167, 2006.
Jaraczewska, et al., Kinesio Taping in Stroke: Improving Functional Use of the Upper Extremity in Hemiplegia, Topics in Stroke Rehabilitation, vol. 13, No. 3, pp. 31-42, 2006.
Dobkin, et al., International Randomized Clinical Trial, Stroke Inpatient Rehabilitation and Reinforcement of Walking Speed (SIR-ROWS) Improves Outcomes, Neurorehabilitation and Neural Repair, vol. 24, No. 3, pp. 235-242, 2010.
Schweighofer, et al., A Functional Threshold for Long-Term Use of Hand and Arm Function Can be Determined: Predictions from a Computational Model and Supporting Data from the Extremity Constraint-Inducted Therapy Evaluation (EXCITE) Trial, Physical Therapy, vol. 89, No. 12, pp. 1327-1336, 2009.
Raab, et al., Magnetic Position and Orientation Tracking System, . . . and Electronic Systems, No. 5, pp. 709-718, 1979.
Simone, et al., Measuring Finger Flexion and Activity Trends over a 25 Hour Period Using a Low Cost Wireless Device, Conference Proceedings, Annual International Conference of the IEEE Engineering in Medicine and Biology Society, IEEE Engineering in Medicine and Biology Society, Conference, vol. 1, pp. 6281-6284, Jan. 2006.
Meijer, et al., Methods to Assess Physical Activity with Special Reference to Motion Sensors and Accelerometers, IEEE Transactions on Biomedical Engineering, vol. 38, No. 3, 99, 221-229, 1991.
B. O. Brand, Microsensor Integration Into Systems-on-Chip, Proceedings of the IEEE, vol. 94, No. 6, pp. 1160-1176, 2006.
Adamovich, et al., A Virtual Reality-Based System for Hand Diagnosis and Rehabilitation, Presence Teleoperators Virtual Environments, vol. 6, No. 2, pp. 229-240, 2005.
Johnson, et al., Implantable Transducer for Two-Degree of Freedom Join Angle Sensing, IEEE Transactions on Rehabilitation Engineering: A publication of the IEEE Engineering in Medicine and Biology Society, vol. 7, No. 3, pp. 349-359, Sep. 1999.
Kanungo, et al., An Efficient K-Means Clustering Algorithm; Analysis and Implemetnation, IEEE Transactions on Pattern Analysis and Machine Intelligence, vol. 24, No. 7, pp. 881-892, Jul. 2002.
Li, et al., Modeling of Prosthetic Limb Rotation Control by Sensing Rotation of Residual Arm Bone, IEEE Transactions on Bio-Medical Engineering, vol. 55, No. 9, pp. 2134-2142, Sep. 2008.
Zheng, et al., Position-Sensing Technologies for Movement Analysis in Stroke Rehabilitation, Medical and Biological Engineering and Computin, vol. 43, No. 4, pp. 229-240, 2005.
Winstein, et al., Methods for Multisite Randomized Trial to Investigate the Effect of Contraint-Induced Movement Therapy in Improving Upper Extremity Function amoung Adults Recovering from a Cerebrovascular Stroke, Neurorehabilitation and Neural Repair, vol. 17, No. 3, pp. 137-152, Sep. 2003.
Knorr, et al. Quantitative Measures of Funcational Upper Limb Movement in Person after Stroke, Conference Proceedings 2nd International IEEE EMBS Converence on Neural Engineering 2005, pp. 252-255, 2005.
Lincoln, et al., Randomized, Controlled Trial to Evaluate Increased Intensity of Physiotherapy Treatment of Arm Function After Stroke, 1999.
Morris, et al., Shoe-Integrated Sensor System for Wireless Gait Analysis and Real-Time Feedback, Proceedings of the Second Joint 24th Annual Conference and the Annual Fall Meeting of the Biomedical Engineering Society Engineering in Medicine and Biology, vol. 3, pp. 2468-2469, 2002.
Seitz, et al., Spontaneous Arm Movement Activity Assessed by Accelerometry is a Marker for Early Recovery After Stroke, Journal of Neurology, vol. 258, No. 3, pp. 457-463, Mar. 2011.
van der Pas, et al., Assessment of Arm Activity Using Triaxial Accelerometry in Patients with a Stroke, Archives of Physical Medicine and Rehabilitation, vol. 92, No. 9, pp. 1437-1442, Sep. 2011.

(56) References Cited

OTHER PUBLICATIONS

Paulick, et al., StabilitySole: Embedded Sensor Insole for Balance and Gait Monitoring, Methods, pp. 171-177, 2011.
Shepherd, et al., Step Activity Monitor: Increased Accuracy in Quantifying Ambulatory Activity, Journal of Orthopaedic Research, vol. 17, No. 5, pp. 703-708, 1999.
Lorussi, et al., Strain Sensing Fabric for Hand Posture and Gesture Monitoring, IEEE Transactions on Information Technology in Biomedicine, a publication of the IEEE Engineering in Medicine and Biology Society, vol. 9, No. 3, pp. 372-381, Oct. 2005.
Granger, et al., The Emerging Science of Functional Assessment: Our Tool for Outcomes Analysis, Archives of Physical Medicine and Rehabilitation, vol. 79, No. 3, pp. 235-240, 1998.
Taub, et al., The Learned Nonuse Phenomenon: Implications for Rehabilitation, Europa Medicophysica, vol. 42, No. 3, pp. 241-256, Sep. 2006.
Bravata, et al., Using Pedometers to Increase Physical Activity a Systematic Review, Jama the Journal of the American Medical Association, vol. 298, No. 19, pp. 2296-2340, 2007.
Hendelman, et al., Validity of Accelerometry for the Assessment of Moderate Intensity Physical Activity in the Field, Medicine and Science in Sports and Exercise, vo. 32, No. 9, suppl, pp. S442-S449, 2000.
Qin, et al., Wrist Posture Affects Hand and Forearm Muscle Stress During Tapping, Applied Ergonomics, pp. 1-8, Apr. 2013.

\* cited by examiner

SYSTEMS AND METHODS FOR MONITORING HAND AND WRIST MOVEMENT

CROSS-REFERENCE TO RELATED APPLICATION(S)

This application claims priority to U.S. Provisional Application Ser. No. 61/774,881, filed Mar. 8, 2013, which is hereby incorporated by reference herein in its entirety.

NOTICE OF GOVERNMENT-SPONSORED RESEARCH

This invention was made with Government support under grant contract number NIH-R01HD062744-01 awarded by the National Institutes of Health. The Government has certain rights in the invention.

BACKGROUND

Human movement monitoring provides a way to quantitatively assess function without therapist intervention. Knowledge of how individuals use their affected limbs as they interact in an unsupervised environment, such as the home, is critical to evaluating motor function and recovery following an injury or a neurologic event. Moreover, an accurate assessment of movement at home is important to administering appropriate therapy in the clinic and to developing appropriate rehabilitation interventions. Home monitoring also enables the possibility to provide daily quantitative assessment to the user, which can help motivate use of the affected limb.

Questionnaires are commonly used to assess the functionality of upper and lower extremities but provide only a subjective interpretation, which can lead to inconsistent assessment results. Recent advancement of miniaturized electronics and sensors has brought about a surge of devices for at home, unrestrained human monitoring that can quantitatively measure use. Accelerometer-based systems are the most common modality for measuring lower-extremity and upper-extremity movement. Although these systems can be used to estimate the amount of gross movement of the upper extremity, they do not address movement quality and small movements may not be detected. Moreover, because the sensors are worn on the wrist, accelerometry is insensitive to fine movements of the wrist and hand, such as those made when writing or typing.

In the laboratory, sophisticated data gloves, goniometers, and motion-capture systems can be used to quantify use of the wrist and hand. However, such devices are not designed for long-term data logging in an uncontrolled environment. In addition, such devices can be difficult for individuals with a physical impairment to don and doff, may restrict natural movement of the hand, and may be too cumbersome to wear for long periods of time.

In view of the above discussion, it can be appreciated that it would be desirable to have an alternative way to measure specific hand or wrist movements in uncontrolled settings.

BRIEF DESCRIPTION OF THE DRAWINGS

The present disclosure may be better understood with reference to the following figures. Matching reference numerals designate corresponding parts throughout the figures, which are not necessarily drawn to scale.

DETAILED DESCRIPTION

As described above, it would be desirable to have a way to measure specific hand or wrist movements in uncontrolled settings. Described in this disclosure are systems and methods for measuring hand and wrist movements that provide quantitative and qualitative hand, wrist, and arm assessment. Because the systems and methods are unobtrusive, they are suitable for non-clinical applications, including home use. In some embodiments, the system includes monitoring apparatus that a patient user wears, including a magnetic ring that is worn on a finger and a data acquisition unit that is worn on the wrist. As the patient moves his or her hand, sensors within the data acquisition unit store movement data, which can be uploaded to a separate computing device for processing.

In the following disclosure, various specific embodiments are described. It is to be understood that those embodiments are example implementations of the disclosed inventions and that alternative embodiments are possible. All such embodiments are intended to fall within the scope of this disclosure.

As indicated above, disclosed herein are systems and methods for measuring hand and wrist movements that provide quantitative and qualitative hand, wrist, and arm assessment, as well as long-term movement monitoring. As described below, the systems and methods can provide quantitative feedback useful in rehabilitation and can be used by healthcare providers to assess patient movement. In addition, the systems and methods can be used as scientific research tools for studying movement. In some cases, the systems and methods can further be used as a computer or game console input device.

Figure 1:
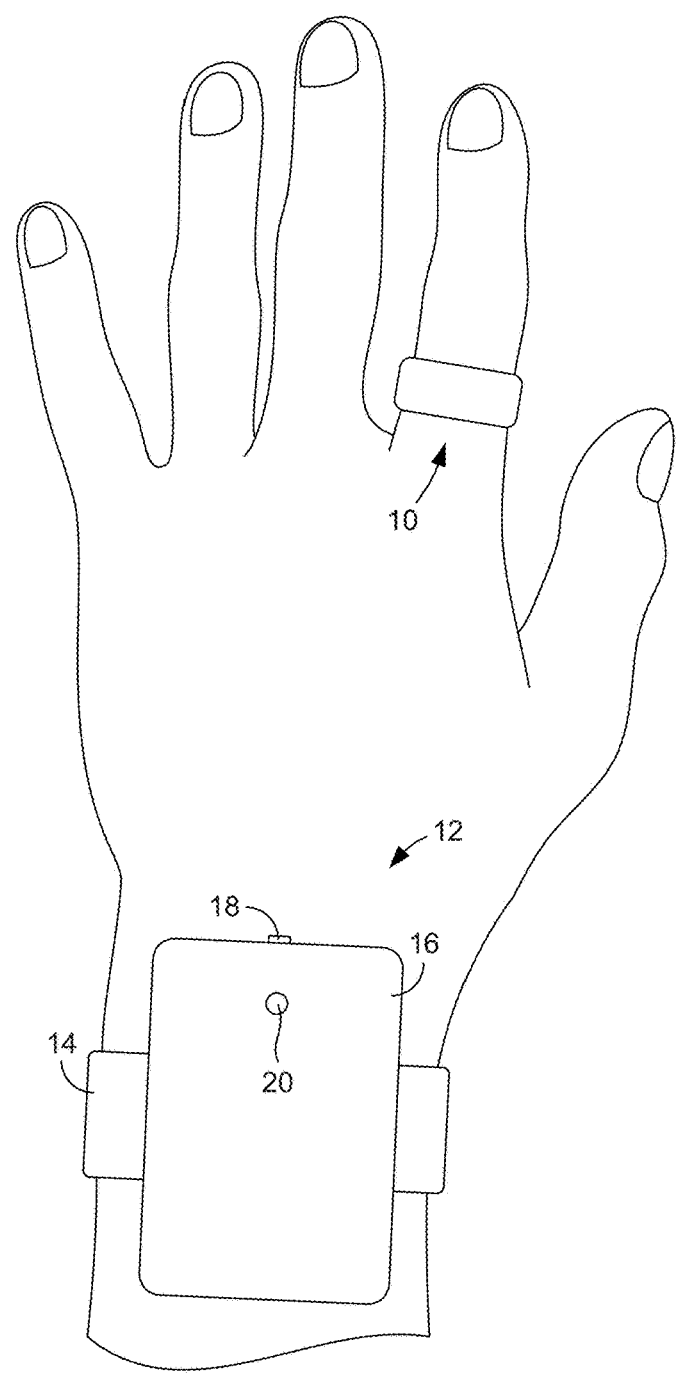
FIG. 1 is a schematic view illustrating an embodiment of apparatus for monitoring hand and wrist movement, the apparatus shown attached to a patient.

FIG. 1 illustrates wearable monitoring apparatus that can be used to collect data about the movement of the patient's hand, wrist, and arm. As shown in FIG. 1, the apparatus includes a ring 10 that is worn on one of the fingers, such as the index finger, and a data acquisition unit 12 that is worn on the wrist in similar manner to a watch. The ring 10 is made of a strongly magnetic material. In some embodiments, the ring 10 comprises a rare-earth magnetic material, such as N50 neodymium, and has a field strength of approximately 0.3 Gauss at a distance of 15 cm (roughly the distance between the metacarpal-phalangeal (MCP) joint of the index finger to the wrist).

In the illustrated example, the data acquisition unit 12 has a generally rectangular housing 16 that is attached to a wrist strap 14. By way of example, the housing 16 is approximately 2 to 3 inches long, 1 to 3 inches wide, and 0.5 to 1 inch thick. It is to be understood, however, that these are only example dimensions and that other dimensions are possible. Moreover, the housing 16 need not be rectangular. Indeed, the shape of the housing 16 is of little importance as long as it is unobtrusive to the patient. In other embodiments, the housing 16 can comprise a fabric, such as neoprene fabric. In still other embodiments, the housing 16 can be cast in a polymer material, such as silicone or urethane. As is further shown in FIG. 1, the data acquisition unit 12 can include a switch 18 and an indicator light 20, such as a light-emitting diode (LED). The purpose of these components is described below.

Figure 2:
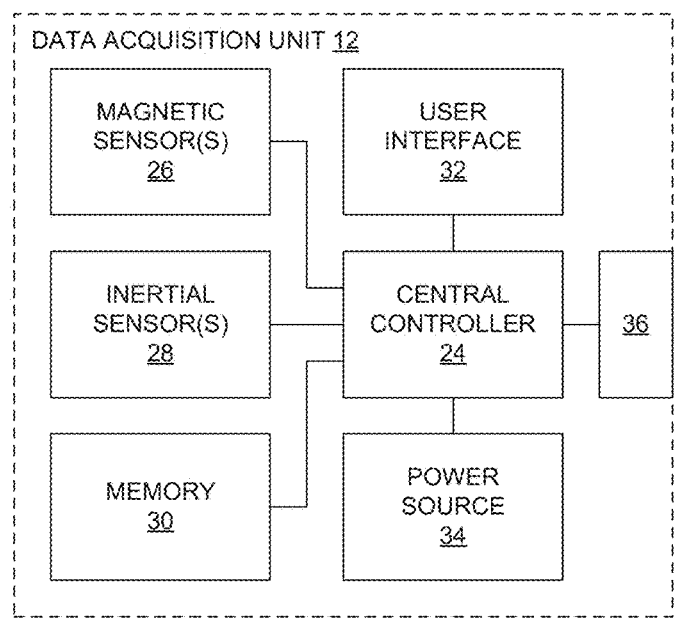
FIG. 2 is a block diagram of an embodiment of a data acquisition unit shown in FIG. 1.

FIG. 2 schematically illustrates an example of electronics housed within the data acquisition unit 12. In this example, the data acquisition unit 12 includes a central controller 24, such as a microcontroller, that controls all operations of the unit. By way of example, the central controller can comprise a PIC24FJ64GB002 microchip microcontroller available from Microchip Technology, Inc. Also comprised by the data acquisition unit 12 are multiple sensors, including one or more magnetic sensors 26 and one or more inertial sensors 28. In some embodiments, the magnetic sensors 26 include one or more pairs of spatially-separated triaxial magnetometers that are positioned at opposite ends of the data acquisition unit 12. The magnetic sensors 26 can measure the strength and orientation of magnetic fields generated by the ring 10 (FIG. 1) as the patient moves his or her hand and wrist. In some embodiments, the magnetic sensors 26 measure the magnetic field strength at a range of +/−3.2 Gauss with 12 bits of resolution. As described below, the measured magnetic field data can be processed to identify specific movements that were performed by the hand or wrist. In some embodiments, the inertial sensors 28 include a triaxial accelerometer that is configured to measure acceleration from movement of the arm to provide further data that can be analyzed.

Although not shown in FIG. 2, the data acquisition unit 12 can include other sensors. For example, the data acquisition unit 12 can comprise one or more of a gyroscopic sensor that can be used to determine limb orientation and a global positioning system (GPS) sensor that can be used to determine the global position of the patient and to obtain a more accurate estimate of arm and hand use.

With further reference to FIG. 2, the data acquisition unit 12 also includes memory 30 that can be used to store the data that is measured by the sensors 26, 28. In some embodiments, the memory 30 is a nonvolatile flash memory, which may or may not be contained within a removable memory card such as a microSD card. By way of example, data can be sampled at a frequency of 25 Hz, in which case 1.8 MB of data are stored to memory 30 per hour. The data acquisition unit 12 further includes a user interface 32, which in this example includes the switch 18 and indicator light 20 shown in FIG. 1.

As is also illustrated in FIG. 2, the data acquisition unit 12 comprises an internal power source 34 such as a battery, which powers the various components of the unit. By way of example, the power source 34 can be a rechargeable 3.7 V, 450 mAh lithium polymer battery. In addition, the data acquisition unit 12 comprises a communication component 36 that enables the unit to communicate with another device, such as a computing device (see FIG. 3). In some embodiments, the communication component 36 comprises a communication port, such as a universal serial bus (USB) port. In other embodiments, the communication component comprises the components that enable wireless communication with the other device, such as a Wi-Fi (IEEE 802.11) or Bluetooth (IEEE 802.15) transmitter and receiver.

It is noted that while specific components are shown in FIG. 2 and have been discussed above, the data acquisition unit 12 can comprise other components. For example, in embodiments in which the power source 34 is a rechargeable battery, the unit 12 would further include a battery recharging circuit.

Figure 3:
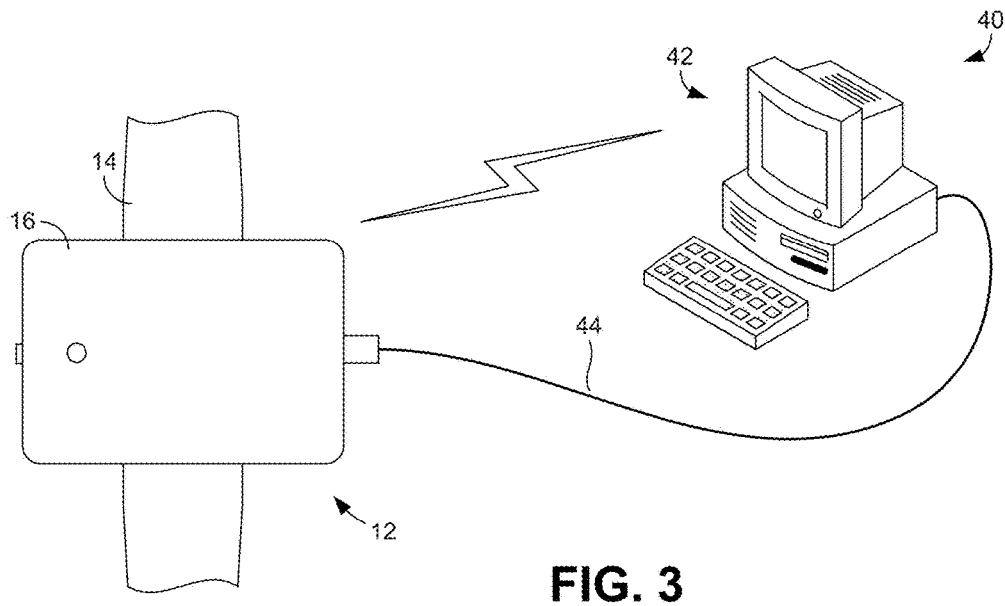
FIG. 3 is a schematic view of an embodiment of a system for monitoring hand and wrist movement that includes the monitoring apparatus of FIG. 1.

Once data has been stored by the data acquisition unit 12, for example, after a day of use, the data can be transmitted to a computing device for processing. FIG. 3 illustrates an example system 40 in which this can occur. As shown in that figure, the system 40 includes the data acquisition unit 12 and a separate computing device 42. The data acquisition unit 12 can transfer its recorded data to the computing device 42 either wirelessly or via a connection cable 44. Although the computing device 42 is illustrated in FIG. 3 as comprising a desktop computer, it is noted that the computing device can be substantially any device that has the ability to receive data from the data acquisition unit 12 and process it in the desired manner. Accordingly, the computing device 42 can alternatively comprise a tablet computer, a smart phone, or another device.

In some embodiments, the system 40 can include a docking station to which the data acquisition unit 12 can be docked. In cases in which the docking station comprises a USB connector to which the data acquisition unit 12 connects, the internal power source 34 can be automatically disconnected and power can be supplied to the unit via the USB connector when the unit is docked. When the docking station is connected the computing device 42, for example, with a wired connection, docking can also automatically initiate downloading of the collected data and recharging of the power source 34.

Figure 4:
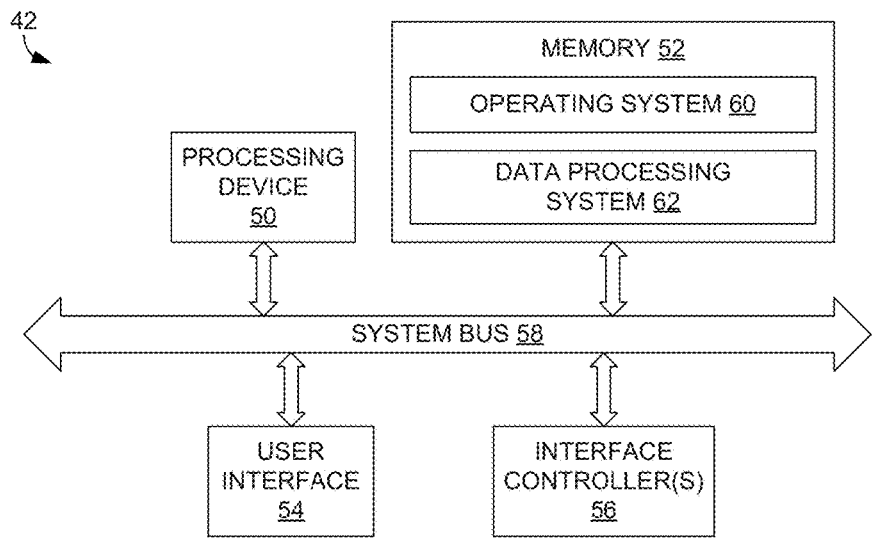
FIG. 4 is a block diagram of an embodiment of a computing device shown in FIG. 3.

FIG. 4 is a block diagram of an example architecture for the computing device 42 shown in FIG. 3. As is shown in FIG. 4, the computing device 42 generally comprises a processing device 50, memory 52, a user interface 54, and interface controllers 56, each of which is connected to a system bus 58.

The processing device 50 can comprise a central computing processor (CPU) that is capable of executing instructions stored within the memory 52. The memory 52 is a non-transitory computer-readable medium that can include any one or a combination of volatile memory elements (e.g., the patient or a random access memory (RAM)) and non-volatile memory elements (e.g., hard disk, flash memory, etc.). The user interface 54 comprises the components with which a user (e.g., healthcare professional) interacts with the computing device 42, such as a keyboard, mouse, and display. The interface controllers 56 comprise the components adapted to facilitate communication with another device, including the data acquisition unit 12.

Stored within memory 52 are various programs and/or algorithms (logic), including an operating system 60 and a data processing system 62. The operating system 60 governs general operation of the computing device 42 while the data processing system 62 is configured to process and analyze the data measured by the data acquisition unit 12 (FIG. 2) to identify specific movements that were made by the patient's hand, wrist, and arm. In some embodiments, the data can be processed to provide information about wrist flexion and extension, ulnar and radial deviation, finger flexion and extension, and gross arm movement.

In some cases, the system 40 can be used to deliver neurologic or muscular rehabilitation to a patient by providing a quantitative measure of their movement. At the end of each day, patients can see how much they have moved their wrists and hands to motivate them to continue using the affected appendage. The system can further be used by healthcare providers as a means to assess human movement. The system can track the quantity and duration of movements throughout the day and can distinguish physical therapy from normal activity. The system can also help determine wrist posture, which is important for assessing, for example, whether or not a patient with carpal tunnel syndrome is typing on a computer keyboard correctly. The system can also be used to answer scientific questions related to human or animal movement. For instance, the relationship between corticospinal tract integrity and quantitative history of movement practice on the response to robot-assisted movement training can be explored.

In addition to enabling evaluation of the patient, the worn monitoring apparatus can also be used as a real-time input device to a computing device or game console. For example, the apparatus can serve as a two-dimensional mouse with a click function. It could also be used as a gaming input device for games, including rehabilitation games for the hand, wrist, or arm.

Having described example embodiments for the systems and apparatuses above, operation and use of the systems and apparatuses will now be discussed. As shown in FIG. 1, the patient user can place the ring 10 on one of his or her fingers, such as the index finger, and can attach the data acquisition unit 12 to his or her wrist using the wrist strap 14. Once those components have been donned, the user can initiate data acquisition by pressing or sliding the switch 18. When the user does this, the indicator light 20 will glow to confirm that the data acquisition unit 12 is recording data. By way of example, data can be continuously recorded for approximately 20 hours.

In some embodiments, the patient can communicate other information to the data acquisition unit 12. For example, the patient can either actuate the switch 18 or a further switch (not shown) to communicate to the unit 12 that the patient is conducting rehabilitation exercises. This mode of operation can be communicated by the indicator light 20 emitting a different color or by a further indicator light (not shown). When the user communicates that he or she is performing exercises, the data collected during that time interval will be tagged so that it can be distinguished from data collected during normal movement.

At the conclusion of the monitoring session, for instance at the end of each day, the patient can remove the data acquisition unit 12 and transmit its collected data to the computing device 42 using a wired or wireless communication channel. Once the data has been received by the computing device 42, it can be processed to identify the movements of one or more of the hand, wrist, and arm. A quantitative and understandable measure of hand, wrist, and/or arm use can then be displayed to the user, who may be the patient or a healthcare professional. Trend analysis that provides a longitudinal assessment of the patient's progress can also be displayed to the user. The results of the data processing can further be transferred to a centralized location (e.g., data server) that can be remotely accessed by researchers and clinicians.

The magnetic field measurements collected by the data acquisition unit 12 inherently reflect the movement of the ring 10. As noted above, it is possible to generate estimates of wrist flexion/extension, wrist radial and ulnar deviation, and finger flexion/extension angles by processing these measurements. Because the strength of the ring's magnetic field measured by the data acquisition unit 12 is comparable to that of the earth, it may be necessary to cancel out the effects caused by the earth's magnetic field. Because the earth's magnetic field does not change much over short distances, whereas the field of the ring 10 does, the earth's magnetic field can be canceled out by taking a differential signal between the two magnetic sensors.

Figure 5:
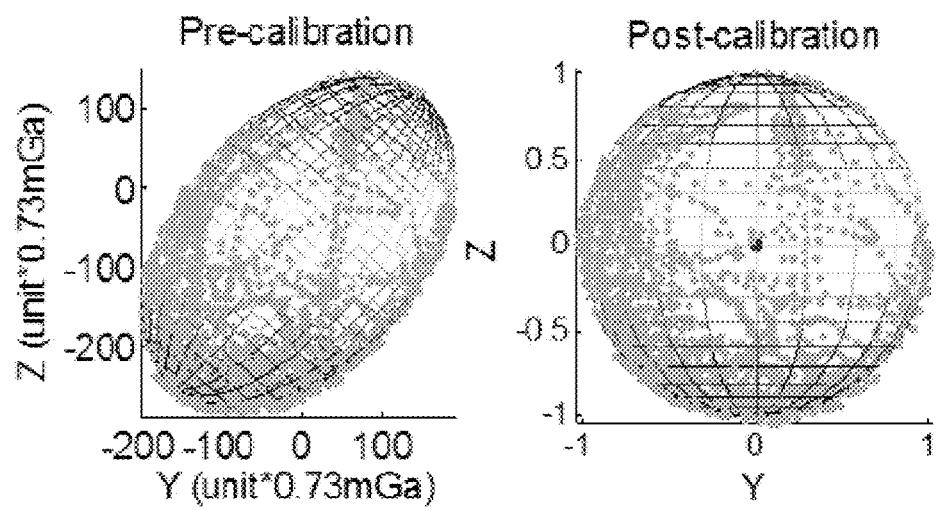
FIG. 5 includes graphs that show uncalibrated and calibrated measurements of a triaxial magnetometer as it was rotated in random orientations for 30 seconds away from ferrous or magnetic materials. The left graph shows a non-symmetrical ellipse about the x, y, and z axes that is a product of magnetic field distortions from ferrous and EMF-producing components on the data acquisition unit printed circuit board, while the right graph shows that, after calibration, signal artifacts are removed and the magnetometer measures the same magnitude regardless of its orientation when mapped in three-dimensional space.

Before taking the differential signal, the magnetic sensors (e.g., magnetometers) are first calibrated to respond uniformly. A perfectly calibrated magnetometer would measure the same vector magnitude for earth's magnetic field regardless of the magnetometer's orientation. However, magnetic distortions caused by ferromagnetic and EMF-producing components located close to the sensors on the data acquisition unit cause them to respond more strongly in some directions than in others. These distortions can be modeled by fitting an ellipsoid to the magnetic field measurements collected by the sensor and using the ellipsoid parameters to translate, scale, and rotate the data such that each sensor's response becomes uniform across all orientations (See FIG. 5).

Figure 6:
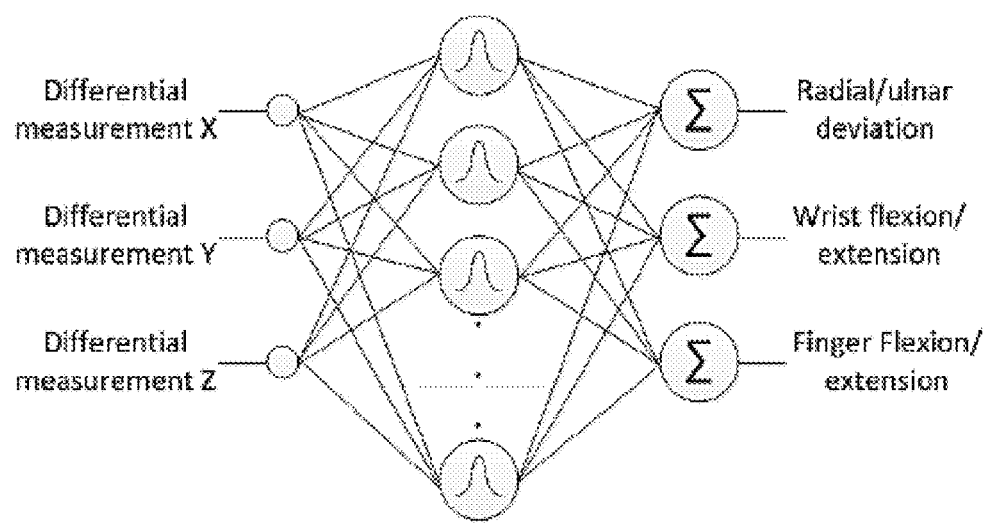
FIG. 6 is a schematic drawing of a 3 input, 3 output radial basis function network (RBFN) that can be used to map magnetometer values to joint angles.

After magnetometer calibration, the three differential measurements can be mapped from the magnetometers to wrist flexion/extension joint angles, wrist radial/ulnar deviation joint angles, and finger flexion angles about the MCP joint. Instead of modeling this relationship analytically, this mapping can be performed using a 3 input, 3 output radial basis function network (RBFN) (see FIG. 6) that is trained from actual data samples because it can incorporate subtle variations in detected field strength caused by ferromagnetic components in the data acquisition unit board that are difficult to model. In some embodiments, the RBFN can comprise an input layer, a single hidden layer holding a bank of 25 nonlinear neurons, and an output layer comprising three linear output neurons. Each of the 25 neurons in the hidden layer can be represented by the Gaussian function $$rbf(x, z, y) = \exp\left(\frac{-(x - \mu_x)^2 - (y - \mu_y)^2 - (z - \mu_z)^2}{\sigma^2}\right) \quad (1)$$

where x, y, and z are the components of our differential measurements, μ(x, y, z) is the center position of the RBF, and σ is the width of the RBF. The output neurons are represented by a weighted linear combination of the output of each RBF.

A combination of supervised and unsupervised learning processes can be used to find values for the widths, center positions, and weights necessary to accurately map magnetometer measurements to corresponding joint angles. During this training process, a goniometric exoskeleton can be attached to the hand while the monitoring apparatus is worn to obtain a "true" measure of joint angles of the finger and wrist. The goniometric exoskeleton has no effect on the magnetometer readings because it contains no ferrous elements. The center positions for the 25 RBFs can be located using a k-means algorithm to identify cluster centers within the differential measurement data. The width of each RBF can be identified by measuring its average distance from its 10 nearest neighbors. Output weights for the RBFs can then be identified using a variation of linear-least-squares optimization known as ridge-regression. Ridge-regression seeks to minimize the least squared error between the model output and the measured data while keeping the weights as small as possible. Penalizing large weights in a controlled way enables reduction of the over-fitting effects in the model. The extent to which large weights are penalized is controlled by a regularization parameter λ. A re-estimation model can be used to find the value for λ that minimizes the generalized cross-validation score of the model.

Unlike walking, in which a step is a relatively well defined, measurable action, there is no standardized action unit of hand use. It can therefore be hypothesized that the total angular distance traveled in wrist flexion/extension, radial/ulnar deviation, and finger flexion extension reflect the amount of use of the hand. To compute the angular distance traveled in each degree of freedom over the course of a usage session, one can calculate the integral of the absolute value of the angular velocity of the data.

A study was performed to determine: (1) the accuracy of the disclosed monitoring apparatus (FIG. 1) in monitoring finger flexion/extension, wrist flexion/extension, and wrist ulnar/radial deviation during a series of range of motion and functional upper-extremity tasks, (2) the accuracy in estimating different levels of movement activity, and (3) the test-retest reliability of these measurements over three separate sessions occurring on separate days using only the initial calibration from the first session. Seven healthy individuals, all males, with an average age of 23.3±3.4 years with no upper-extremity movement disorders participated in the study. The monitoring apparatus was tested on the right hand for all subjects (one of the subjects was left-hand dominant).

The magnetometers were calibrated as described above at the beginning of each testing session. The participants then donned the monitoring apparatus and goniometric exoskeleton and were instructed to move their fingers and wrist randomly through their full range of motion for two minutes. This data was then used to train the RBFN to map magnetometer values to the joint angles measured by the exoskeleton. Participants were then instructed to complete a set of 12 tasks three times at either a low, medium, or high intensity. Subjects were randomly assigned to experience the three intensity conditions in random order. The set of tasks that the participants were instructed to complete at the low intensity condition were:

1. Simulate eating of ten small crackers, one at a time.
2. Flex and extend your fingers through your maximum range of motion ten times.
3. Move 30 standard index playing cards, one at a time.
4. Take five bills and ten coins out of a provided wallet and put the money back in the wallet, one at a time.
5. Open and close a door eight times.
6. Pour 6 oz. of water from one 16 oz. cup into an identical 16 oz. cup spaced 12 inches apart eight times.
7. Perform radial and ulnar deviation through your maximum range of motion ten times.
8. Tie/untie the shoelaces of a provided shoe three times.
9. Type the phrase "The quick brown fox jumped over the lazy dogs" six times.
10. Lay your hand and arm flat on the table and remain still.
11. Flex and extend your wrist through your maximum range of motion ten times.
12. Write the phrase "The quick brown fox jumped over the lazy dogs" three times.

For the medium intensity condition, participants were instructed to make twice as many repetitions as in the low intensity condition, and for the high intensity condition they performed three times as many repetitions. For example, participants simulated eating 20 small crackers in the medium intensity condition and 30 small crackers in the high intensity condition. Subjects completed the same tasks in the same order for all intensity conditions varying only the quantity of movement. They completed a total of three sessions spaced 1 to 2 days apart between Sessions 1 and 2, and 6 to 8 days apart between Sessions 2 and 3.

In order to match for the duration of each task for the three conditions, subjects were allotted one and a half minutes to complete each task. This duration was selected to give the subjects enough time to complete the specified number of repetitions in the high intensity condition. In the common event that a task was completed before time expired, subjects were asked to lay their hand and arm flat on the table and remain still. In the rare event that the task was not completed before the allotted time, subjects were instructed to finish the task. A computer program guided the participants through each task by displaying how to complete the task and the amount of time remaining for the given task. A trained individual provided supplementary guidance and helped count the number of repetitions remaining in each task.

Joint angle estimates from the monitoring apparatus and goniometric exoskeleton were first low-pass filtered using a 6th order Butterworth filter with a cutoff frequency of 2 Hz. The joint angular velocities were then calculated by calculating the derivative of the joint angle estimates. The distance traveled in wrist flexion/extension, radial/ulnar deviation, and finger flexion/extension were then estimated by integrating the absolute value of the estimated joint angular velocities.

Figure 7:
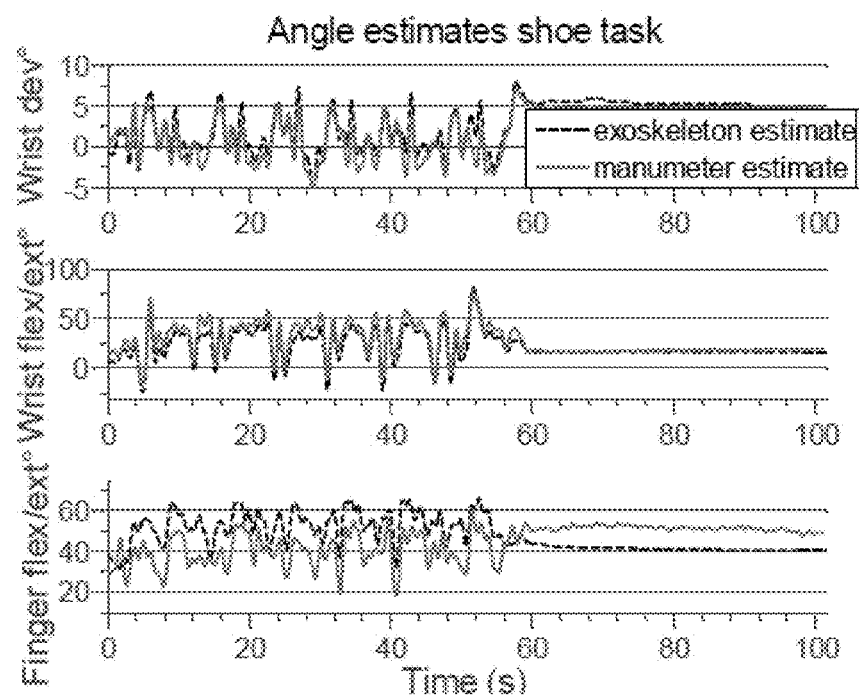
FIG. 7 includes graphs of angle estimates obtained while a subject performed a shoe tying task at the medium intensity condition for radial/ulnar deviation (top graph), wrist flexion/extension (middle graph), and finger flexion/extension (bottom graph) on Day 1. The solid line represents the monitoring apparatus' joint angle estimates and the dashed line represents goniometric exoskeleton angle estimates.
Figure 8:
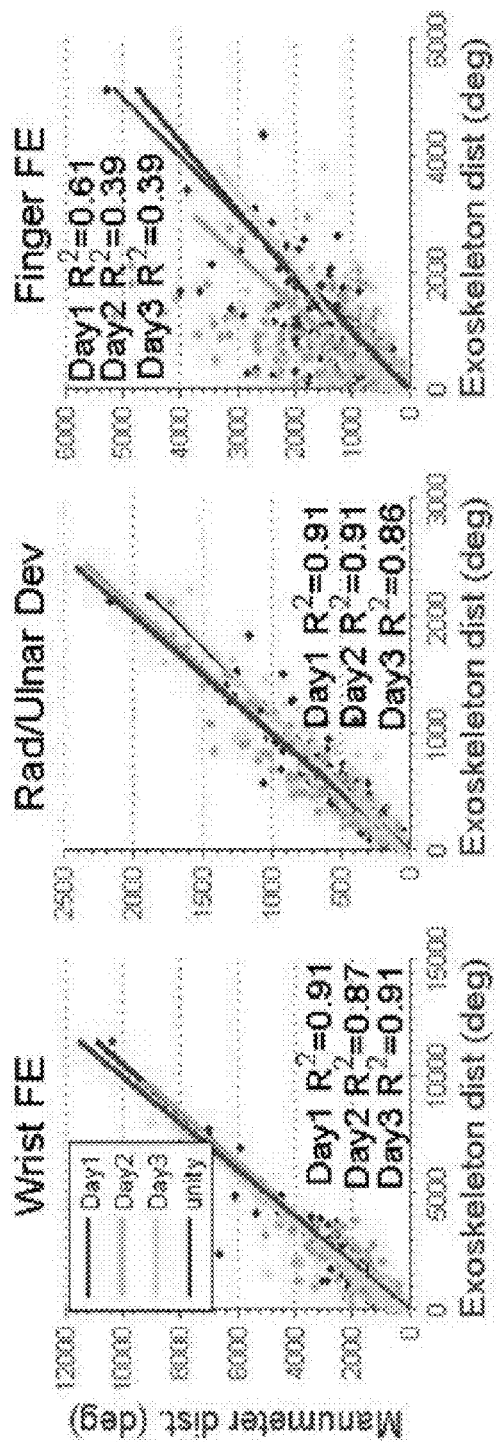
FIG. 8 includes graphs of estimates of the total angular distance measured by the monitoring apparatus and the goniometric exoskeleton for wrist flexion/extension (Wrist FE, left), radial/ulnar deviation (Wrist Dev., middle), and finger flexion/extension (Finger FE, right).

The estimates obtained using the inventive monitoring apparatus correlated well with the exoskeleton estimates of the joint angles (see FIG. 7). The correlation between the monitoring apparatus and the exoskeleton angular distance traveled estimates had a $R2$ value around 0.9 for wrist flexion/extension and wrist radial/ulnar deviation across all three days, including the session that occurred a week later, with all correlations being highly significant ($P<0.0001$) (see FIG. 8). The correlations were still significant for finger flexion, but the R2 values were smaller.

Figure 9:
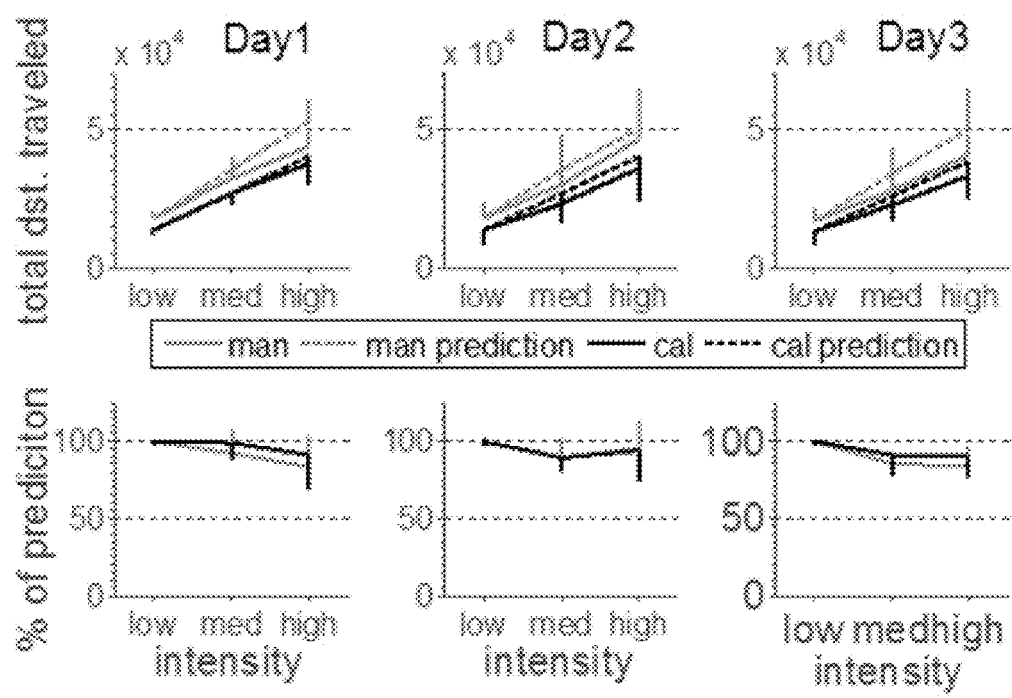
FIG. 9 includes graphs of the total angular distance summed across all 12 tasks and all three joint angles at each intensity condition for Day 1 (left), Day 2 (middle, 2-3 days later) and Day 3 (right, 6-8 days later). Data from the monitoring apparatus and the goniometric exoskeleton are shown by the solid light and dark lines, respectively, while the dashed lines show predictions calculated by doubling and tripling the values measured at the low intensity condition. The bottom graphs show the distance-traveled estimates as a percentage of their predicted values.

To determine whether or not the monitoring apparatus could detect the amount of hand use in a fixed period in which it is worn, the total angular distance traveled for all tasks completed for all joints at each intensity condition was summed. Since the design of the experiment mandated that the amount of movement in the low intensity condition should double and triple in the medium and high intensity conditions, predicted values were defined for the monitoring apparatus and exoskeleton by doubling and tripling their distance traveled estimates at the low intensity condition. The estimates obtained from the monitoring apparatus were on average about 80% of their predicted values including at the 6-8 day post follow up session. The error was comparable to the exoskeleton error (FIG. 9), indicating that the apparatus was as sensitive to changes in movement intensity as the more obtrusive, "gold standard".

There was a small, consistent offset in the estimate of the monitoring apparatus with respect to that of the goniometric exoskeleton. In practice, this offset could be measured during the initial calibration of the device on Day 1 for each subject, and then subtracted for the following days. Therefore, the offset from the first 12 tasks on Day 1 of the experiment were calculated and that offset was applied to all intensity conditions on all days. With the offset correction applied to the estimates, the total distance traveled summed across all tasks, all conditions, and all joint angles were on average 92.5%±28.4, 98.3%±23.3, and 94.7%±19.3 of the exoskeleton estimates for Day 1, Day 2, and Day 3 respectively.

In calibration process described above, a unique calibration can be performed for each individual who uses the monitoring apparatus. One alternative to such a calibration method is to create a large bank of calibrations and then select from that bank a calibration that was generated using a process such as that described above that appears to be the best match for each particular user. Given that the calibration method described above maps values collected in the magnetometer input space into joint angle estimates, the more similar a user's input space is to the magnetometer data used to create a particular calibration, the more likely that the calibration will provide good joint angle estimates for the user.

The amount of similarity between the user's magnetometer input space and that of a bank calibration can be found by first defining features of the input space (such as its center position, orientation, extents, etc.) and then computing the distance in this new feature space between the user's data and each of the calibrations being evaluated. The larger the bank of calibrations is and the more areas of the possible magnetometer input space that it covers, the more likely it will be that an effective calibration can be found.

The invention claimed is:

1. A system for monitoring hand or wrist movement, the system comprising:
   monitoring apparatus including a magnetic ring comprising a band configured to wrap around a single finger of a user and a data acquisition unit adapted to be worn on a wrist of the user, the data acquisition unit including a magnetic sensor that is configured to measure the strength and orientation of magnetic fields generated by the ring, an inertial sensor that is configured to measure accelerations of the user's arm, memory that is configured to store the data collected by the sensors, a central controller that is configured to control operation of the data acquisition unit including storing the collected data to the memory and transmitting the collected data to a separate computing device, and a battery that powers the data acquisition unit; and
   a computing device that executes a data processing system configured to generate from the data collected by the monitoring apparatus estimates of wrist flexion and extension, wrist radial and ulnar deviation, and finger flexion and extension angles, wherein the data processing system is configured to estimate wrist flexion and extension, wrist radial and ulnar deviation, and finger flexion and extension angles using a trained radial basis function network.

2. The apparatus of claim 1, wherein the band is an endless band of rare-earth magnetic material.

3. The apparatus of claim 2, wherein the band is made of neodymium.

4. The apparatus of claim 1, wherein the data acquisition unit includes a pair of spatially-separated magnetic sensors.

5. The apparatus of claim 4, wherein the magnetic sensors are triaxial magnetometers.

6. The apparatus of claim 1, wherein the inertial sensor is a triaxial accelerometer.

7. The apparatus of claim 1, wherein the data acquisition unit further includes a wireless transmitter for transmitting data collected by the sensors to the computing device.

8. The apparatus of claim 1, wherein the data acquisition unit further includes a wrist strap adapted to wrap around the patient's wrist.

9. The system of claim 1, wherein the band comprises an endless band of magnetic material.

10. The system of claim 1, wherein the band is circular.

11. The apparatus of claim 1, wherein the data acquisition unit further includes a gyroscopic sensor that is configured to determine arm orientation.

12. The apparatus of claim 1, wherein the data acquisition unit further includes a global positioning system (GPS) sensor that is configured to determine the global position of the user.

13. The system of claim 1, wherein the radial basis function network comprises nonlinear neurons represented by the Gaussian function $$rbf(x, z, y,) = \exp\left(\frac{-(x-\mu_x)^2 - (y-\mu_y)^2 - (z-\mu_z)^2}{\sigma^2}\right)$$

where x, y, and z are the components of differential magnetic sensor measurements, $\mu(x, y, z)$ is the center position of the radial basis function of the network, and $\sigma$ is the width of the radial basis function.

* * * * *